United States Patent [19]

Wing

[11] 4,180,079

[45] Dec. 25, 1979

[54] ELECTROACUPUNCTURE INSTRUMENT

[76] Inventor: Thomas W. Wing, 380 E. Baseline Rd., Claremont, Calif. 91711

[21] Appl. No.: 887,003

[22] Filed: Mar. 16, 1978

[51] Int. Cl.$^2$ .................. A61H 39/00; A61N 1/36

[52] U.S. Cl. .................. 128/422; 128/801; 128/803; 128/907

[58] Field of Search ............ 128/2.1 C, 2.1 R, 303.13, 128/303.18, 405, 406, 407, 408, 409, 410, 411, 417, 419 R, 421, 422, 734, 735, 787–789, 800, 801, 803, 907

[56] References Cited

U.S. PATENT DOCUMENTS

| 1,684,859 | 9/1928 | Catlin | 128/409 |
| 3,207,151 | 9/1965 | Takagi | 128/2.1 C |
| 3,516,413 | 6/1970 | McDonald et al. | 128/422 |
| 3,755,900 | 9/1973 | Friedman | 128/2.1 R X |
| 3,859,983 | 1/1975 | Dohring et al. | 128/2.1 R |
| 3,991,755 | 11/1976 | Vernon et al. | 128/409 X |
| 4,102,348 | 7/1978 | Hihara et al. | 128/422 |

FOREIGN PATENT DOCUMENTS

| 2634401 | 1/1978 | Fed. Rep. of Germany | 128/421 |
| 376028 | 10/1930 | Italy | 128/409 |
| 997670 | 7/1965 | United Kingdom | 128/2.1 R |
| 1126634 | 9/1968 | United Kingdom | 128/2.1 R |
| 1416141 | 12/1975 | United Kingdom | 128/2.1 C |

Primary Examiner—Lee S. Cohen
Attorney, Agent, or Firm—Gene W. Arant

[57] ABSTRACT

An electroacupuncture instrument is powered by self-contained batteries and is of sufficiently small size to be held in the hand of a user. A probe terminating in a moist wad of cotton is the active electrode which applies an electrical pulse to a selected portion of the skin. The instrument case is the other electrode towards which current flows in a return path through the hand that is holding the instrument.

4 Claims, 6 Drawing Figures

ELECTROACUPUNCTURE INSTRUMENT

BACKGROUND OF THE INVENTION

In recent decades a medical technique has been developed for applying electrical pulses to the skin of a patient, at locations selected in accordance with the precepts of the ancient art of acupuncture, but without using the traditional needles that pierce the skin. The theory and technique of this development were described in my recent book entitled "THE THEORY OF APPLIED ELECTROACUPUNCTURE", by Dr. Thomas W. Wing, published Jan. 27, 1976 by O-Matic, Inc., 902 East Holt Avenue, Pomona, California 91767. A number of articles relating to electroacupuncture have also appeared in recent issues of the American Journal of Acupuncture, published at 1400 Lost Acre Drive, Felton, California 95018.

Instruments heretofore available for carrying out electroacupuncture treatments have included a pair of movable electrodes, which must be handled by the attending doctor, one being provided for the return current path and the other being provided as the active electrode for applying an electrical pulse to selected points on the skin of the patient. Many patients are now able to treat themselves, acting under instructions from their doctor. A need has therefore arisen for an electroacupuncture instrument that is specifically designed for self-treatment.

SUMMARY OF THE INVENTION

According to one feature of the invention an electroacupuncture instrument is specifically designed for purpose of self-treatment, and is housed in a case that is adapted to be held in the hand of the user, with the case itself providing the electrode for the return current.

According to another feature of the invention electrical pulses of different frequencies and different amplitudes are combined in a novel manner, providing beneficial results to the patient.

According to another feature of the invention there is provided a skin probe of improved construction, which facilitates the periodic replacement of an ear swab used as an operative part of the probe.

DRAWING SUMMARY

DESCRIPTION OF INSTRUMENT

(FIGS. 1-4)

Figure 1:
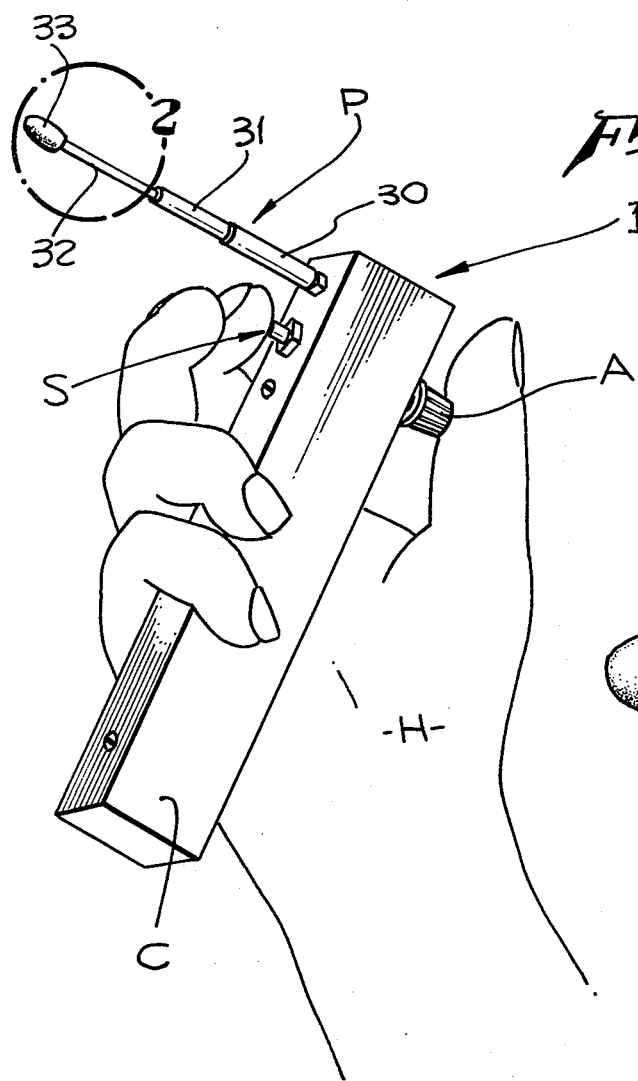
FIG. 1 is a perspective view of my electroacupuncture instrument held in the hand of a user.

My new instrument I includes a metallic housing or case C which is sufficiently small to be held in the hand H of a user, as shown in FIG. 1. The case is about six inches in length and is of rectangular cross-section, being about an inch wide and an inch thick. At one end of the case, being the upper end as shown in FIG. 1, a probe P extends perpendicularly outward from one wall of the case. A switch S for controlling energization of the internal circuitry is located on the same wall of the case immediately beneath the probe. On the other side of the case, opposite the switch S, is an amplitude control knob A for controlling the amplitude of the electrical impulse that is supplied to the probe P.

Figure 3:
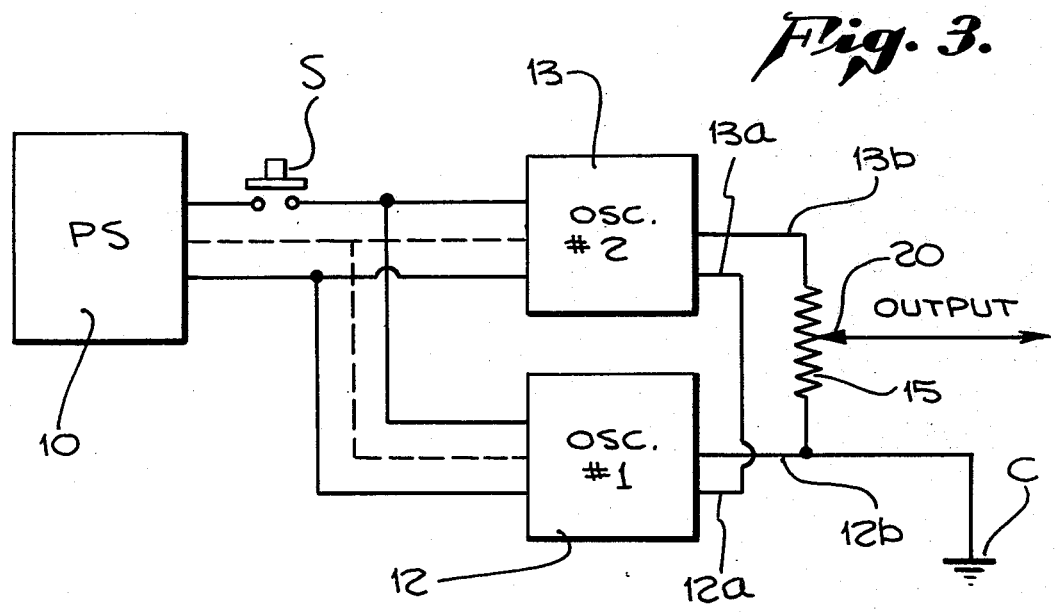
FIG. 3 is a schematic diagram, partially in block form and partially in two-line form, of the complete electrical circuit of the instrument.

As shown in FIG. 1, switch S is suitably located where it may be operated by the forefinger of the user's hand. Switch S includes a depressable switch member that is supported on a compression spring and the switch member is normally out of engagement with its associated contact, as shown in FIG. 3. Thus, the pulse generating circuit is normally not energized, but will be energized during the intervals of time when the switch S remains depressed.

As shown in FIG. 3 a power supply circuit 10 includes batteries that are contained within the case C. Energy from the power supply circuit is supplied to the inputs of both a first oscillator 12 and a second oscillator 13. Closing of switch S energizes both of these oscillators at the same time. A first output terminal 12a of the oscillator 12 is connected directly to a first output terminal 13a of oscillator 13. An output resistor 15 is connected between the second output 12b of oscillator 12 and the second output 13b of oscillator 13. Therefore, a composite voltage signal appears across resistor 15 which represents the difference between the output voltage signal generated by oscillator 12 and that generated by oscillator 13.

Resistor 15 is engaged by a variable tap 20, which is used to select what portion of the voltage appearing across the resistor 15 will be supplied to the probe P. At one end of resistor 15 a ground connection is made from output terminal 12b of oscillator 12 to the case C. Movable contact 20 is electrically connected to the probe P, and specifically element 31 thereof, which therefore carries the output voltage relative to the case C.

Figure 2:
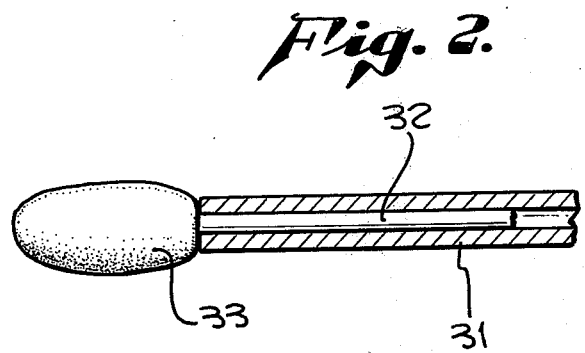
FIG. 2 is a detail view of the probe, partially in cross-section, taken within the circle 2 of FIG. 1.

The outer wall of case C is made of metal. Part of the structure of probe P is a conventional electrical jack 30 that includes concentric inner and outer parts. The inner part, not specifically shown, is electrically connected to the movable contact 20. The outer part of jack 30 is attached to case C. The two parts of the jack are insulated from each other. A tubular metallic extension member 31 shown in FIG. 2, is removably supported within the jack 30 where it is insulated from the outer part of the jack but in electrically conductive engagement with the inner part of the jack.

A conventional ear swab commonly known as a Q Tip includes a rigid stem 32 having a wad of cotton 33 fastened to one end thereof. Rigid stem 32 is received in the hollow interior of tubular extension 31. It will be noted, however, that the extension is longer than the stem.

During operation of the instrument the wet cotton wad 33 is placed in contact with a selected portion of the skin of the patient. The case of housing C is pushed slightly towards the skin, causing cotton wad 33 to remain in good electrically conductive engagement with the outer end of tubular extension member 31. Therefore, current flows from output resistor 15 through movable contact 20, the interior part of jack 30, tubular extension member 31, the wetted cotton wad 33, and the body of the patient, back to the metallic housing of the case C which, as shown by FIG. 3, is electrically synonymous with output terminal 12b of oscillator 12.

From time to time it is necessary to replace the ear swab. This is easily done even if the cotton wad 33 has been broken off from the stem 32. Tubular extension member is removed from the jack 30, and a needle or the like is used to expel the rigid stem 32. Then a new ear swab is inserted in member 31.

Figure 4:
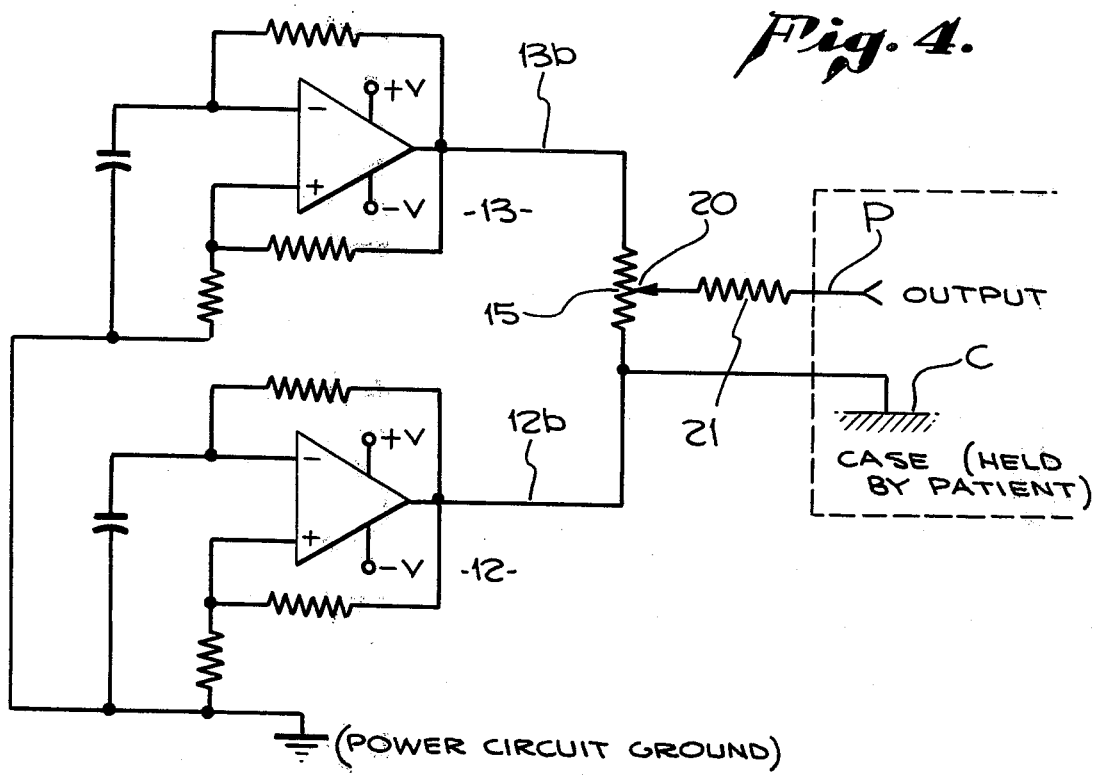
FIG. 4 is a schematic diagram in two-line form of the pulse generating circuit of the instrument.

FIG. 4 shows the electrical circuit diagram of the pulse generating circuit in more detail. As there indicated, the reference or ground connection for the power supply circuit does not coincide with the case or housing C. In FIG. 4 a resistor 21 is shown connected between probe P and movable contact 20, and this resistor 21 represents the equivalent resistance of the entire probe circuit out to and including the cotton wad 33.

MODE OF OPERATION

The first oscillator 12 is designed to operate at a relatively low frequency of 0.25 Hertz. It produces a square-wave voltage of several volts amplitude. The frequency and amplitude of this oscillator are not adjustable.

Second oscillator 13 also produces a square wave output voltage, but at higher frequency. Its frequency is variable within the range of 0.6 Hertz to 320 Hertz. The means for adjusting the frequency of oscillator 13, although not specifically shown, is entirely conventional. The output voltage of oscillator 13 is of smaller magnitude than the output voltage of oscillator 12, for example, one-half.

Figure 5:
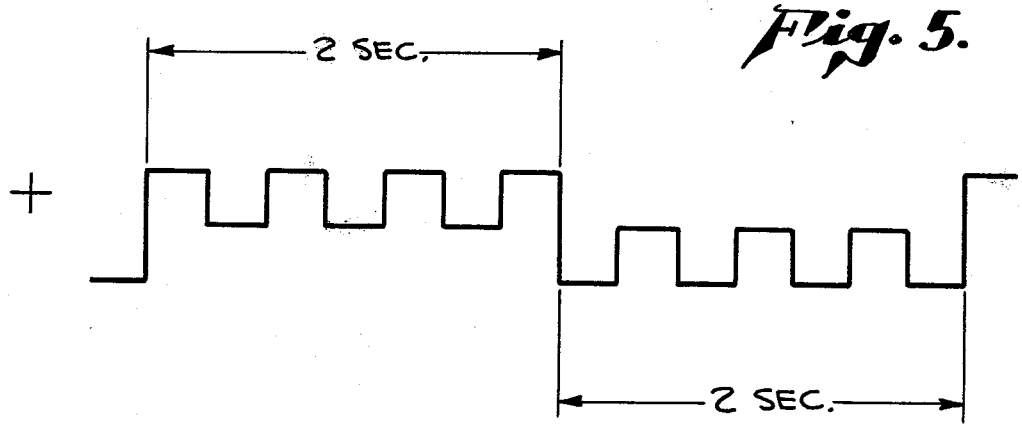
FIG. 5 shows a typical output voltage wave form of the instrument, when not loaded by coupling to the patient.

FIG. 5 illustrates the typical output voltage of the electrical pulse generating circuit which appears across the output resistor 15, when probe P is not in contact with the skin of the patient. The entire voltage wave form is relatively high for two seconds, which is half the period of oscillator 12, and then is relatively low for the following two seconds. While earlier in this description the statement has been made that it is the difference between the output voltage signals of the two oscillators which appears across resistor 15, it will nevertheless be seen that due to the frequency differences between the two oscillators the concept of difference or subtraction is tenuous at best, and hence in practical effect the voltage developed across resistor 15 is the sum of the two oscillator output voltages.

Figure 6:
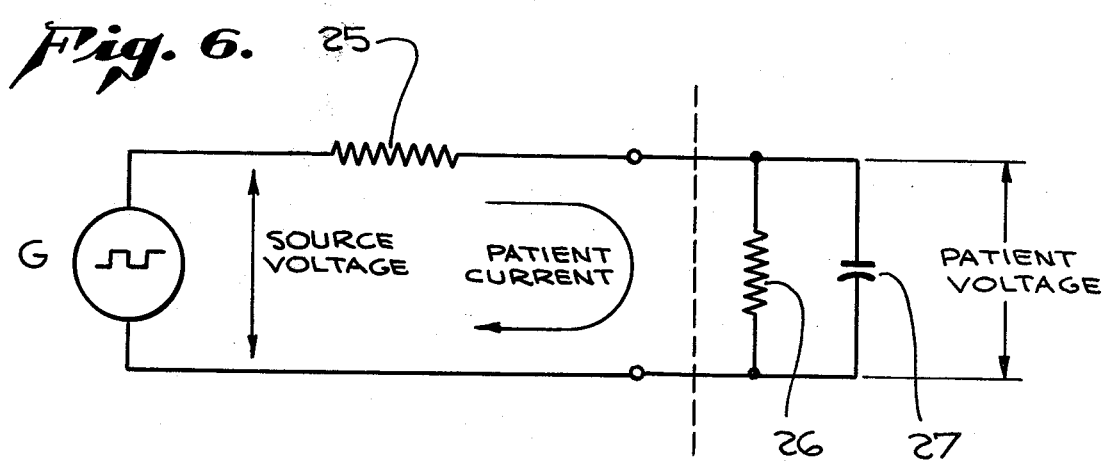
FIG. 6 is an equivalent electrical circuit of the instrument and patient, when the instrument is coupled to the patient.

FIG. 6 illustrates the equivalent circuit of the instrument when probe P is engaging the patient's skin. G represents an equivalent generator that produces the composite output of the two oscillators. A resistor 25 is the equivalent internal resistance of the two oscillators, and also including the equivalent series loop resistance of the output resistor 15. A resistor 26 represents the equivalent of the resistance of the body of the patient. A capacitor 27 represents the equivalent electrical capacitance of the body of the patient.

Electrical operation of the instrument as applied to the patient is best understood by considering FIGS. 5 and 6 together. The precisely square wave forms of FIG. 5 are significantly distorted under load, particularly being rounded at the leading edges because of the equivalent capacitance of the patient's body. Application of the voltage wave causes a charge to build up in one direction across capacitor 27 for a period of two seconds. Then the applied voltage is reversed and the accumulated charge is first drained off and then built up in the opposite polarity. At the very same time, smaller amplitude and higher frequency variations are taking place in response to the portion of the voltage wave that is attributable to the high frequency oscillator 13. The application of this type of composite wave form has proved beneficial in the treatment of patients.

ALTERNATE FORMS

Although a specific form of instrument has been illustrated herein which is adapted for self-treatment, it will be understood that the use of two oscillators of different amplitudes and frequencies is not thus restricted, but may also extend to the traditional type of electroacupuncture instrument having two movable probes whose operation is controlled by the attending doctor.

While my improved probe structure has also been illustrated in conjunction with an instrument designed specifically for self-treatment, it will likewise be understood that this feature of the invention may be used in conjunction with an instrument of the more traditional type.

The invention has been described in considerable detail in order to comply with the patent laws by providing a full public disclosure of at least one of its forms. However, such detailed description is not intended in any way to limit the broad features or principles of the invention, or the scope of patent monopoly to be granted.

What is claimed is:

1. An electroacupuncture instrument comprising, in combination:

metallic housing means of such size and configuration as to be conveniently grasped within one hand of the user and in surface-to-surface contact with at least about a square inch of the skin surface thereof;

a pulse generating circuit within said metallic housing means including a low-frequency oscillator adapted to produce essentially a square-wave output signal, a high frequency oscillator adapted to produce essentially a square-wave output signal, the output signal of said low-frequency oscillator being of substantially greater amplitude than the output signal of said high-frequency oscillator, one of the output terminals of each of said oscillators being connected together, and an output resistor connected between the other output terminals of said two oscillators so that the difference between said two output signals appears across said resistor;

selective means for selecting a portion of said resistor across which to derive a composite output signal of selected amplitude, said selective means having two output terminals, one of said output terminals being connected to said metallic housing means; and probe means connected to the other of said output terminals for applying said composite output signal to the skin of a patient.

2. The instrument of claim 1 wherein the amplitude of said low-frequency output signal is approximately double the amplitude of said high-frequency output signal.

3. The instrument of claim 1 wherein the frequency of said low-frequency output signal is about 0.25 Hertz and the frequency of said high-frequency output signal is variable in the range of about 0.6 Hertz to about 320 Hertz.

4. An electroacupuncture instrument comprising, in combination:

an electrical jack having two concentric, mutually insulated electrically conductive parts;

a metal case connected to the outer part of said jack;

a tubular metallic extension member having inner and outer ends, its inner end being attached to said jack inner part in conductive engagement therewith;

pulse generating circuit means within said metal case and connected between said metal case and said jack inner part; and an ear swab including a rigid stem and a wad of cotton fastened to one end of said stem, said wad of cotton being removably supported upon the outer end of said extension member while said stem is received in the hollow interior thereof;

whereby said wad of cotton may be wetted to act as the skin-engaging portion of said probe, and after use may be replaced without replacing said jack or said extension member.

* * * * *